(12) United States Patent
Cox

(10) Patent No.: US 7,572,288 B2
(45) Date of Patent: Aug. 11, 2009

(54) ANEURYSM TREATMENT DEVICE AND METHOD OF USE

(75) Inventor: Brian J. Cox, Laguna Niguel, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 09/909,715

(22) Filed: Jul. 20, 2001

(65) Prior Publication Data

US 2003/0018294 A1   Jan. 23, 2003

(51) Int. Cl.
*A61F 2/06* (2006.01)

(52) U.S. Cl. .................................... 623/1.17; 623/1.15

(58) Field of Classification Search ................ 623/1.11, 623/1.44, 1.46, 1.15, 1.16, 1.17, 1.19, 1.2; 606/191, 192, 194, 198
See application file for complete search history.

(56) References Cited

U.S. PATENT DOCUMENTS

| 4,512,338 | A |   | 4/1985  | Balko et al. |
| 4,655,771 | A |   | 4/1987  | Wallsten |
| 4,733,665 | A |   | 3/1988  | Palmaz |
| 4,941,870 | A |   | 7/1990  | Okada et al. |
| 4,994,069 | A |   | 2/1991  | Ritchart et al. |
| 5,015,253 | A |   | 5/1991  | MacGregor |
| 5,162,430 | A |   | 11/1992 | Rhee et al. |
| 5,226,911 | A |   | 7/1993  | Chee et al. |
| 5,234,456 | A | * | 8/1993  | Silvestrini .................... 623/1.2 |
| 5,258,042 | A | * | 11/1993 | Mehta ......................... 600/36 |
| 5,389,106 | A |   | 2/1995  | Tower |
| 5,410,016 | A |   | 4/1995  | Hubbell et al. |
| 5,464,449 | A |   | 11/1995 | Ryan et al. |
| 5,514,379 | A | * | 5/1996  | Weissleder et al. .......... 424/426 |
| 5,514,380 | A |   | 5/1996  | Song et al. |
| 5,536,274 | A |   | 7/1996  | Neuss |
| 5,609,628 | A |   | 3/1997  | Keranen |
| 5,609,629 | A | * | 3/1997  | Fearnot et al. ............. 623/1.42 |
| 5,630,829 | A |   | 5/1997  | Lauterjung |
| 5,674,241 | A | * | 10/1997 | Bley et al. .................... 623/1.2 |
| 5,674,295 | A | * | 10/1997 | Ray et al. ................. 623/17.12 |

(Continued)

FOREIGN PATENT DOCUMENTS

EP   1 266 631 A1   12/2002

(Continued)

OTHER PUBLICATIONS

MedicineNet.com; http:/www.medterms.com/script/main/Art.asp?AricleKey=9942; printed Oct. 23, 2203; included to demonstrate the pH human blood.*

(Continued)

*Primary Examiner*—Darwin P Erezo
(74) *Attorney, Agent, or Firm*—Inskeep IP Group, Inc.

(57) ABSTRACT

The present invention is directed to aneurysm treatment devices which are capable of being delivered to the situs of a vascular aneurysm through a catheter. The treatment devices comprise, in general, an expandable stent having fenestrations and a reactive material selectively applied to not all of the fenestrations. The reactive material has a non-reacted state and a reacted state and the reactive material in the reacted state is capable of increasing the resistance to blood flow through said fenestrations.

12 Claims, 9 Drawing Sheets

U.S. PATENT DOCUMENTS

| | | | |
|---|---|---|---|
| 5,741,325 | A | 4/1998 | Chaikof et al. |
| 5,749,894 | A | 5/1998 | Engelson |
| 5,750,585 | A | 5/1998 | Park et al. |
| 5,769,882 | A * | 6/1998 | Fogarty et al. ............... 128/898 |
| 5,785,965 | A | 7/1998 | Pratt et al. |
| 5,800,454 | A | 9/1998 | Jacobsen et al. |
| 5,823,198 | A | 10/1998 | Jones et al. |
| 5,843,089 | A * | 12/1998 | Sahatjian et al. ............ 623/1.11 |
| 5,911,717 | A | 6/1999 | Jacobsen et al. |
| 5,911,731 | A | 6/1999 | Pham et al. |
| 5,935,148 | A | 8/1999 | Villar et al. |
| 5,941,249 | A | 8/1999 | Maynard |
| 5,951,599 | A | 9/1999 | McCrory |
| 5,980,514 | A | 11/1999 | Kupiecki et al. |
| 5,980,550 | A | 11/1999 | Eder et al. |
| 5,980,554 | A | 11/1999 | Lenker et al. |
| 5,990,237 | A | 11/1999 | Bentley et al. |
| 6,015,431 | A * | 1/2000 | Thornton et al. ............ 623/1.14 |
| 6,036,720 | A | 3/2000 | Abrams et al. |
| 6,060,534 | A * | 5/2000 | Ronan et al. ................. 523/113 |
| 6,063,111 | A | 5/2000 | Hieshima et al. |
| 6,090,911 | A * | 7/2000 | Petka et al. .................. 530/300 |
| 6,093,199 | A * | 7/2000 | Brown et al. ................. 606/200 |
| 6,113,629 | A | 9/2000 | Ken |
| 6,120,847 | A | 9/2000 | Yang et al. |
| 6,140,127 | A | 10/2000 | Sprague |
| 6,152,144 | A | 11/2000 | Lesh et al. |
| 6,165,193 | A | 12/2000 | Greene, Jr. et al. |
| 6,168,592 | B1 | 1/2001 | Kupiecki et al. |
| 6,168,615 | B1 | 1/2001 | Ken et al. |
| 6,176,240 | B1 | 1/2001 | Nikolchev et al. |
| 6,177,095 | B1 | 1/2001 | Sawhney et al. |
| 6,184,266 | B1 | 2/2001 | Ronan et al. |
| 6,187,370 | B1 | 2/2001 | Dinh et al. |
| 6,190,402 | B1 | 2/2001 | Horton et al. |
| 6,193,708 | B1 | 2/2001 | Ken et al. |
| 6,201,065 | B1 | 3/2001 | Pathak et al. |
| 6,224,892 | B1 | 5/2001 | Searle |
| 6,238,403 | B1 | 5/2001 | Greene, Jr. et al. |
| 6,264,695 | B1 * | 7/2001 | Stoy ........................ 623/17.16 |
| 6,280,457 | B1 | 8/2001 | Wallace et al. |
| 6,309,367 | B1 | 10/2001 | Boock |
| 6,364,893 | B1 * | 4/2002 | Sahatjian et al. ............ 606/194 |
| 6,398,808 | B1 * | 6/2002 | Palasis ....................... 623/1.46 |
| 6,419,686 | B1 | 7/2002 | McLeod et al. |
| 6,551,303 | B1 | 4/2003 | Van Tassel et al. |
| 6,554,849 | B1 | 4/2003 | Jones et al. |
| 6,569,179 | B2 | 5/2003 | Teoh et al. |
| 6,569,190 | B2 | 5/2003 | Whalen, II et al. |
| 6,596,296 | B1 * | 7/2003 | Nelson et al. ............... 424/426 |
| 6,605,111 | B2 | 8/2003 | Bose et al. |
| 6,605,294 | B2 * | 8/2003 | Sawhney .................... 424/426 |
| 6,613,073 | B1 | 9/2003 | White et al. |
| 6,613,074 | B1 | 9/2003 | Mitelberg et al. |
| 6,663,607 | B2 | 12/2003 | Slaikeu et al. |
| 6,786,876 | B2 * | 9/2004 | Cox ........................... 600/585 |
| 2001/0000188 | A1 * | 4/2001 | Lenker et al. .............. 623/1.13 |
| 2002/0013618 | A1 | 1/2002 | Marotta et al. |
| 2002/0026228 | A1 | 2/2002 | Schauerte |
| 2002/0049495 | A1 | 4/2002 | Kutryk et al. |
| 2002/0123789 | A1 | 9/2002 | Francis et al. |
| 2003/0004531 | A1 | 1/2003 | Jones et al. |
| 2003/0023190 | A1 | 1/2003 | Cox |
| 2003/0055451 | A1 | 3/2003 | Jones et al. |
| 2003/0120300 | A1 | 6/2003 | Porter |
| 2003/0139802 | A1 | 7/2003 | Wulfman et al. |
| 2003/0171739 | A1 | 9/2003 | Murphy et al. |
| 2004/0111112 | A1 | 6/2004 | Hoffmann |
| 2004/0172056 | A1 | 9/2004 | Guterman et al. |

FOREIGN PATENT DOCUMENTS

| | | |
|---|---|---|
| WO | WO 95/17859 | 7/1995 |
| WO | WO 98/50102 A1 | 11/1998 |
| WO | WO 99/02092 | 1/1999 |
| WO | WO 9905977 A1 | 2/1999 |
| WO | WO 99/59479 A1 | 11/1999 |
| WO | WO 99/62429 A1 | 12/1999 |
| WO | WO 99/62432 A1 | 12/1999 |
| WO | WO 99/65397 A1 | 12/1999 |
| WO | WO 00/04845 A2 | 2/2000 |
| WO | WO 0007524 A1 | 2/2000 |
| WO | WO 00/13593 A1 | 3/2000 |
| WO | WO 00/18321 | 4/2000 |
| WO | WO 0032112 A1 | 6/2000 |
| WO | WO 00/44306 A1 | 8/2000 |
| WO | WO 00/56247 A1 | 9/2000 |
| WO | WO 00/57818 A1 | 10/2000 |
| WO | WO 00/74577 A1 | 12/2000 |
| WO | WO 01/01890 A1 | 1/2001 |
| WO | WO 0103607 A2 | 1/2001 |
| WO | WO 01/37892 A1 | 5/2001 |
| WO | WO 01/41676 A1 | 6/2001 |
| WO | WO 02/05731 A1 | 1/2002 |
| WO | WO 02/080782 A1 | 10/2002 |
| WO | WO 02087472 | 11/2002 |
| WO | WO 03/077984 A1 | 9/2003 |

OTHER PUBLICATIONS

Schmitz-Rode et al., "Self-expandable Spindle for Transcatheter Vascular Occlusion: In Vivo Experiments", Radiology, Jul. 1993, vol. 188, pp. 95-100.

Massoud, T.F., Turjman, F., JI, C., Vinuela, F., Guglielmi, G., Gobin, Y.P. and Duckwiler, G.R., "*Endovascular Treatment of Fusiform Aneurysms with Stents and Coils: Technical Feasibility in a Swine Model*," AJNR 16: 1953-1963, Nov. 1995.

Szikora, I., Guterman, L.R., Wells, K.M., and Hopkins, L.N., "*Combined Use of Stents and Coils to Treat Experimental Wide-Necked Carotid Aneurysms: Preliminary Results*," AJNR 15:1091-1102, Jun. 1994.

Ahuja, A.A., Hergenrother, R. W., Strother, C.M., Rappe, A.A., Cooper, S.L., and Graves, V.B., "*Platinum Coil Coatings to Increase Thrombogenicity: A Preliminary Study in Rabbits*," AJNR 14:794-798, Jul./Aug. 1993.

Weber, J., M.D., "*Techniques and Results of Therapeutic Catheter Embolization of Congenital Vascular Defects*," Int Angiol, vol. 9:214-223, 1990.

Vinuela, F., M.D., Duckwiler, G., M.D., and Mawad, M., M.D., "*Guglielmi Detachable Coil Emoblization of Acute Intracranial Aneurysm: Perioperative Anatomical and Clinical Outcome in 403 Patients*," J. Neurosurg 86:475-482, 1997.

Klee, D., Weiss, N., Lovenich, W., Lahann, J., Reul, J. and Hocker, H., "*Bioactive Coating of Platinum Surfaces for Embolization Coils*," © 2000 Society for Biomaterials, Sixth World Biomaterials Congress Transactions, p. 215.

Whitelock, J., Poole-Warren, L., Yu, W. and Underwood, A., "*Perlecan Coating of Vascular Grafts Enhances Endothelial Cell Growth*," © 2000 Society for Biomaterials, Sixth World Biomaterials Congress Transactions, p. 953.

Raymond, J., M.D., Desfaits, A.C., PhD., and Roy, D., M.D., "Fibrinogen and Vascular Smooth Muscle Cell Grafts Promote Healing of Experimental Aneurysms Treated by Embolization," printed from website http://www.strokeaha.org, pp. 1657-1664, © 1999 American Heart Association, Inc.

Dawson, R., M.D., Krisht, A., M.D., Barrow, D., M.D., Joseph, G., M.D., Shengelaia, G., M.D., and Bonner, G., M.B.A., "*Treatment of Experimental Aneurysms Using Collagen-Coated Microcoils*," Neurosurgery, 36:133-140, 1995.

Turjman, F., Massoud, T., JI, C., Guglielmi, G., Vinuela, F. and Robert, J., "*Combined Stent Implantation and Endosaccular Coil Placement for Treatment of Experimental Wide-Necked Aneurysms: A Feasibility Study in Swine,*" AJNR 15:1087-1990, Jun. 1994.

Post, J., M.D., Cardelli, J., M.D., Wilson, R., M.D., Griffith, J., DVM, Fox, P., M.D., Waybill, P., M.D. and Hills, J., "*Experimental Nonsurgical Transcervical Sterilization with a Custom-Designed Platinum Microcoil,*" Journal of Vascular and Interventional Radiology, vol. 8:13-118, Jan.-Feb. 1997.

Wakhloo, A., M.D., Ph.D., Lanzino, G., M.D., Lieber, B., Ph.D., Hopkins, L.N., M.D., "Stents for Intracranial Aneurysms: The Beginning of a New Endovascular Era?" Neurosurgery, vol. 43, No. 2, Aug. 1998, pp. 377-379.

Lownie, S., Pelz, D., Fox, A., "*Endovascular Therapy of a Large Vertebral Artery Aneurysm Using Stent and Coils,*" Canadian Journal of Neurological Sciences, vol. 27, No. 2, May 2000, pp. 162-165.

Kalra, G.S., Verma, P.K., Singh, S., Arora, R., "*Transcatheter Closure of Ventricular Septal Defect Using Detachable Steel Coil,*" Heart, 1999; 82:395-396.

* cited by examiner

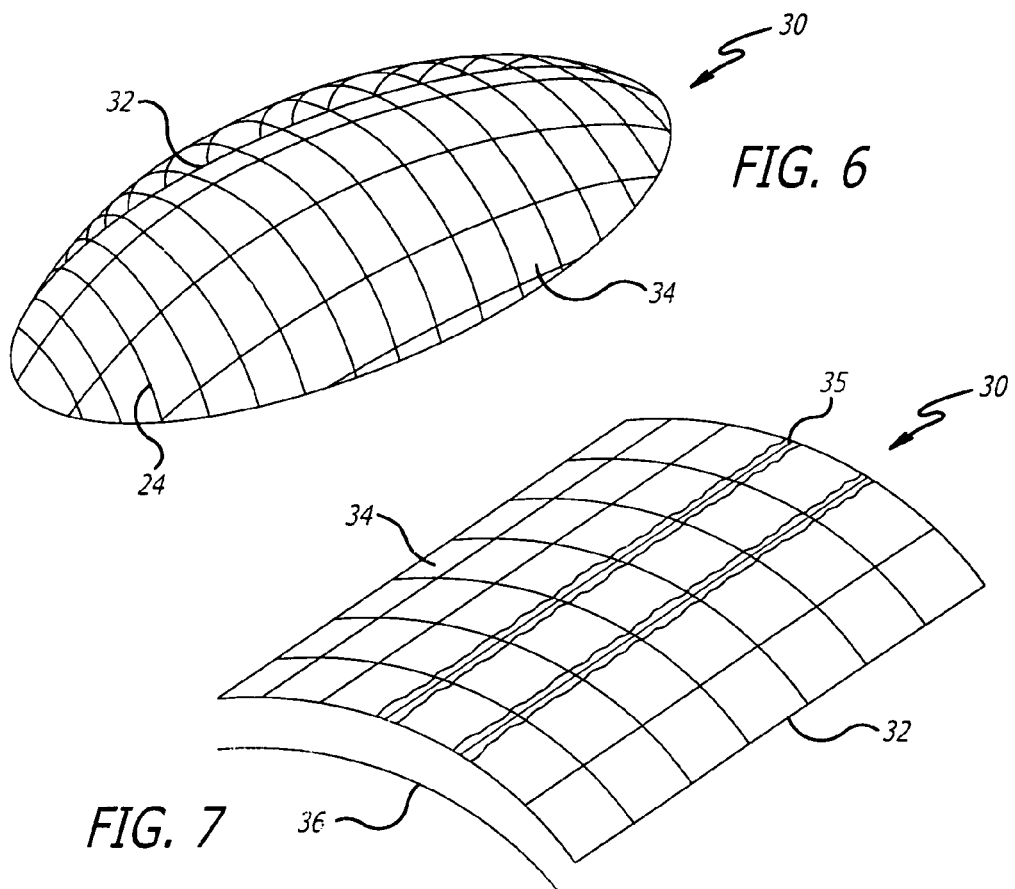
FIG. 6
FIG. 7
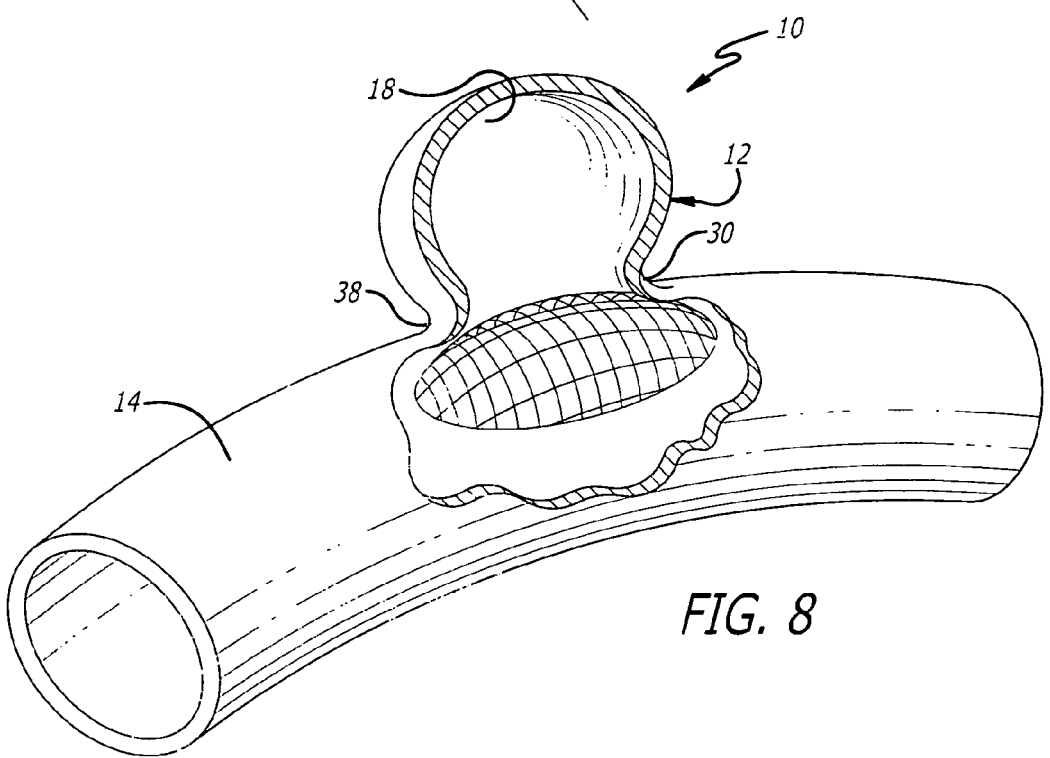
FIG. 8

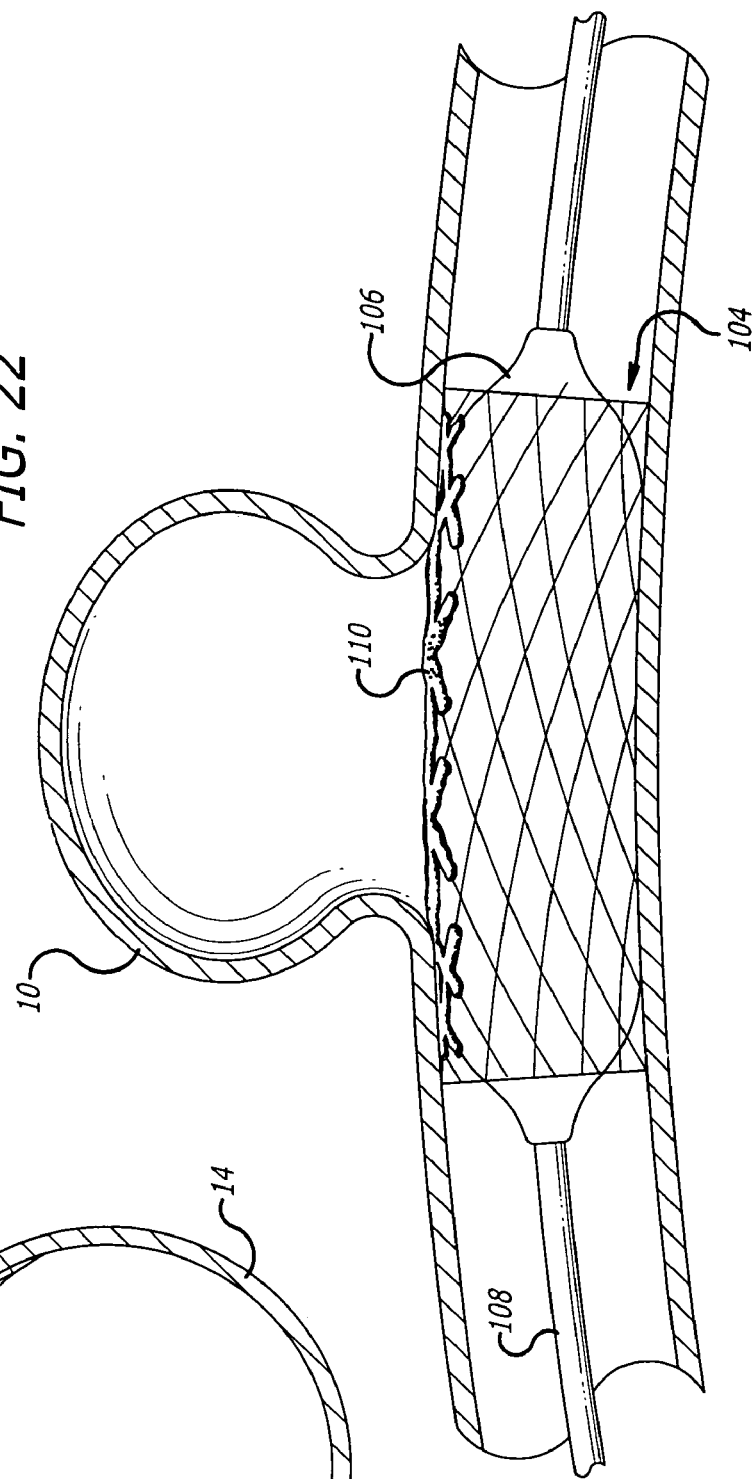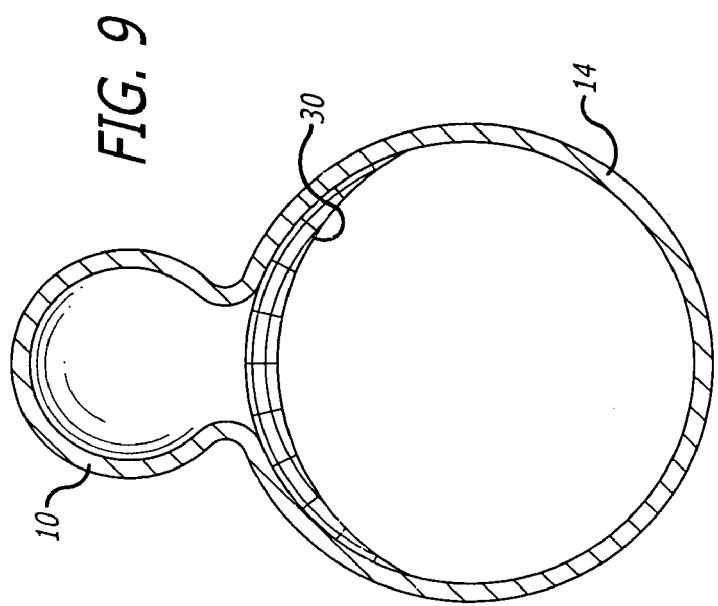

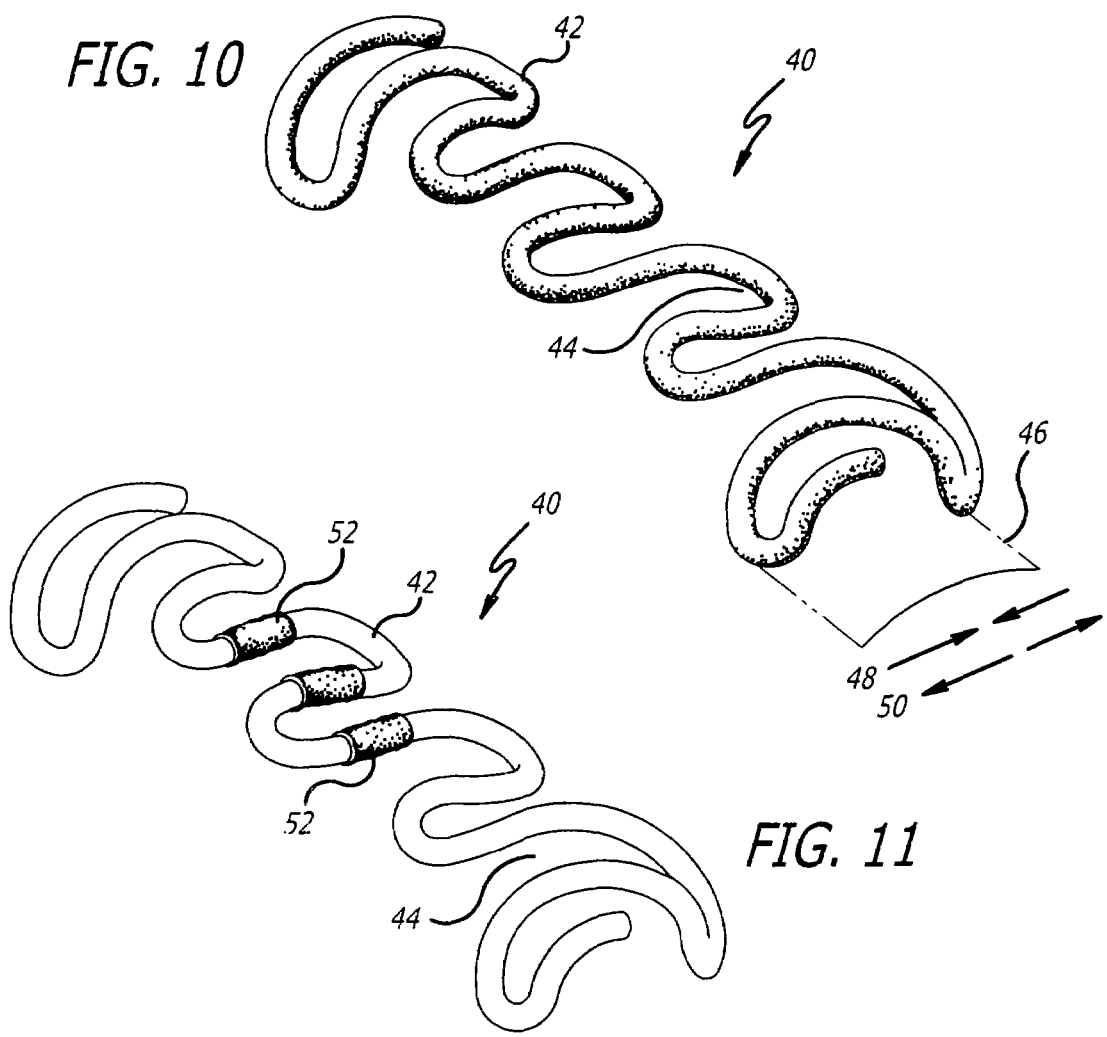
FIG. 10
FIG. 11
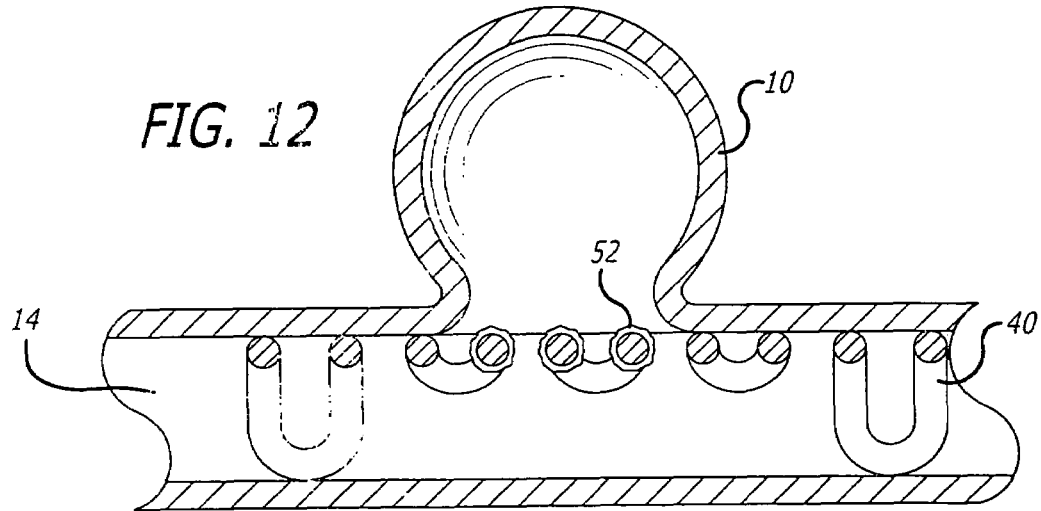
FIG. 12

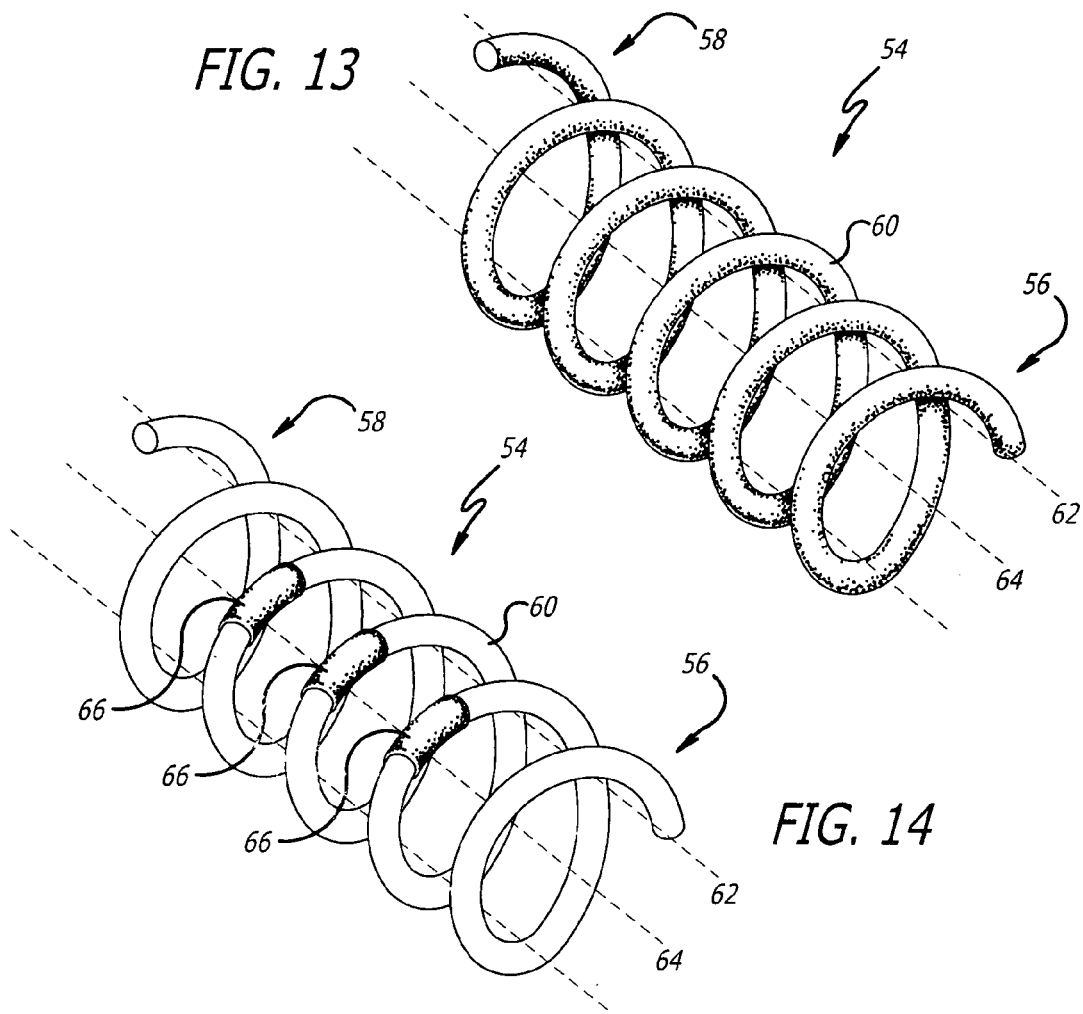
FIG. 13
FIG. 14
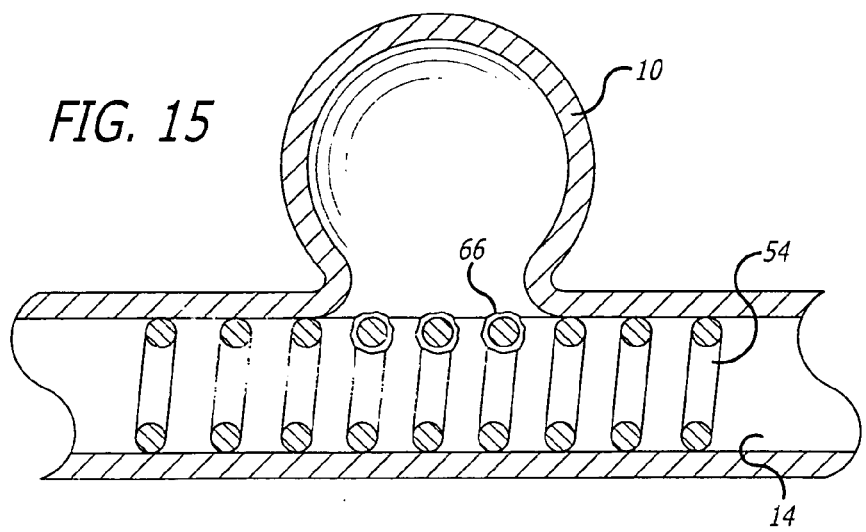
FIG. 15

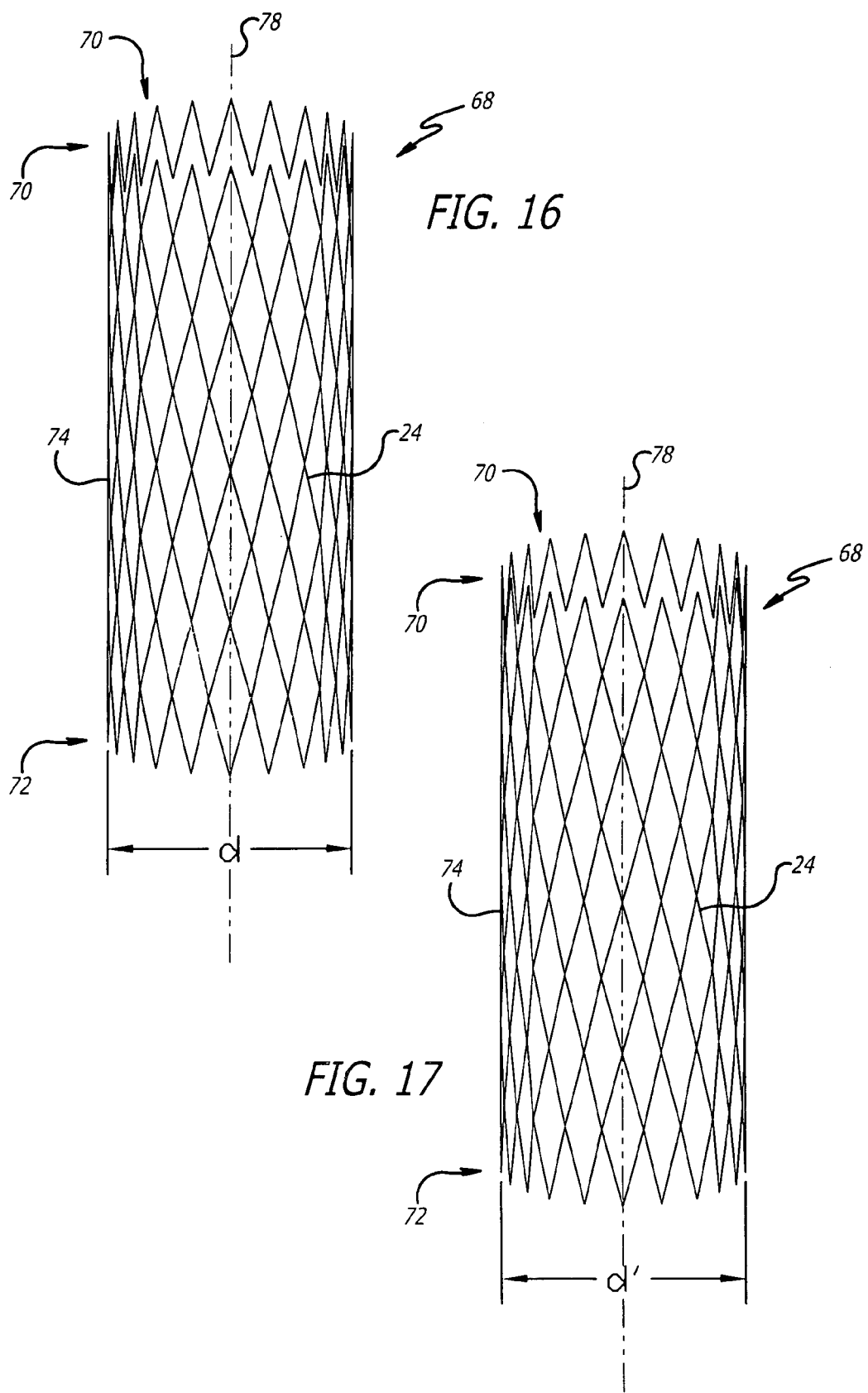

ANEURYSM TREATMENT DEVICE AND METHOD OF USE

CROSS REFERENCE TO RELATED APPLICATIONS

The entire contents of U.S. patent application Ser. No. 09/804,935, entitled "Hydrogels That Undergo Volumetric Expansion In Response To Changes In Their Environment And Their Methods Of Manufacture And Use", filed on Mar. 13, 2001 naming Gregory M. Cruise and Michael J. Constant as co-inventors, is hereby incorporated by this reference.

BACKGROUND OF THE INVENTION

Generally, the mammalian circulatory system is comprised of a heart, which acts as a pump, and a system of blood vessels which transport the blood to various points in the body. Due to the force exerted by the flowing blood on the blood vessel the blood vessels may develop a variety of vascular disabilities or dysfunctions. One common vascular dysfunction, commonly known as an aneurysm, results from the abnormal widening of the blood vessel. Typically, vascular aneurysms are formed as a result of the weakening of the wall of a blood vessel and subsequent ballooning of the vessel wall. As shown in FIG. 1, the aneurysm 10 often comprises a narrow neck portion 12 which is in communication with the blood vessel 14 and a dome portion 16 in communication with the neck portion 12. As shown in FIG. 1 the neck portion 12 and the dome portion 16 form a cavity 18. Aneurysms have been known to form in a plurality of locations though the body, including, for example, the brain, the abdomen, and throughout the circulatory system.

In response, several surgical techniques for treating aneurysms have been developed. Initially, an aneurysmectomy was required to repair the dysfunctional tissue. The aneurysmectomy procedure requires the surgeon to gain access to the aneurysm, excise the aneurysm, and replace the void with a prosthetic graft. Because this is a major surgical undertaking, the mortality rate of the procedure is relatively high. Commonly, the aneurysmectomy procedure is unavailable to patients with severe coronary or cerebral arteriosclerosis, severe restrictive pulmonary disease, and significant renal disease or other complicating factors.

An alternate method of treating cerebral aneurysms called 'microsurgical clipping' requires the placement of a metallic clip across the neck of the aneurysm, thereby excluding the aneurysm from the blood flow.

In response to the shortcomings of the aneurysmectomy and the microsurgical clipping procedures, less invasive methods of treatment have been developed. Commonly, these procedures require the formation of an artificial vaso-occlusion, which is obtained by implanting a number of devices or suitable materials into the cavity 18 of the aneurysm, thereby resulting in a decrease in the flow of blood into the aneurysm. The reduced flow results in hemostasis and the formation of a clot. Generally, this procedure requires the surgeon to advance a micro-catheter to a location inside the aneurysm and deposit a biologically-compatible vaso-occlusive material or device therein. Typical vaso-occlusive devices and materials include platinum micro-coils, hog hair, microfibrillar collagen, various polymeric agents, material suspensions, and other space filling materials. FIG. 2 shows an aneurysm 10 formed on a blood vessel 14, the aneurysm 10 having a vaso-occlusive device 20 positioned within the aneurysm dome 18. A disadvantage of filling an aneurysm with devices is that the vaso-occlusive mass may impinge on nerves or other biological structures, thereby resulting adverse biological symptoms. For example, the impingement of the vaso-occlusive device 20 on structures or nerves within the brain, commonly known as 'mass effect', may result in adverse neurological symptoms. Another problem associated with vaso-occlusive devices is maintaining the device within the aneurysm. Blood flow through an otherwise functional blood vessel may be compromised should the device migrate from the aneurysm during or following implantation, thereby possibly resulting in a vascular embolism.

An alternate method of repairing an aneurysm has been developed which requires the implantation of a mechanical support device within the blood vessel near the neck portion of the aneurysm. Generally, these mechanical support devices, commonly referred to as "stents" comprise deployable mechanical support structures capable of delivery to a situs within the blood vessel through catheters. In addition to providing mechanical support to the dysfunctional vessel wall, the stent may include a mechanical structure which seeks to restrict the blood flow though the portion of the blood vessel proximate the aneurysm, thereby reducing or eliminating the aneurysm. Exemplary mechanical structures capable of restricting blood flow to an aneurysm include meshes or fenestrated structures which are positioned near an aneurysm 10 and restrict the flow of blood thereto. FIG. 3 shows a stent 22 positioned in a blood vessel 14 proximal to an aneurysm 10. While a stent may provide adequate mechanical support to the blood vessel, these devices have demonstrated limited effectiveness in limiting blood flow to the aneurysm. As such, the aneurysm typically remains intact and may increase in size. In response, stents may be covered with various coatings designed to limit blood flow to the aneurysm. These coatings typically include biologically compatible polymers, films, and fabrics. However, the application of these coatings to the stents increases the cross-sectional diameter of the device, thereby resulting in a high profile stent-graft. As a result, the blood flow through the blood vessel is reduced by the presence of a high profile stent-graft. In addition, device profile is a significant problem for the treatment of cerebral aneurysms due to the small size of the cerebral blood vessels, therefore requiring the device to be deliverable to the aneurysm through a micro-catheter. As such, high profile stent-grafts are typically not used in the treatment of cerebral aneurysms.

Thus, there is presently a need for a device and method for effectively treating aneurysms without significantly affecting blood flow through the blood vessel.

BRIEF SUMMARY OF THE INVENTION

The present invention solves the aforementioned problems in that the aneurysm treatment device of the present invention effectively occludes or inhibits blood flow to an aneurysm without substantially impairing blood flow through the blood vessel. In addition, the aneurysm treatment device of the present invention is capable of being applied to a plurality of aneurysms formed on blood vessels throughout the body. Those skilled in the art will appreciate that the present invention is easy to manufacture and may be manufactured from a plurality of materials.

The aneurysm treatment device of the present invention comprises at least one support member and reactive material selectively applied to the support member. The at least one support member, which has at least a first surface capable of receiving the reactive material, provides a substrate for receiving the reactive material. Alternatively, the at least one support member may also provide support to weakened vascular tissue. The reactive material has a non-reacted state and a reacted state. In a reacted state the reactive material, as selectively applied to the at least one support member, is capable of restricting or occluding the flow of blood to the aneurysm. In one embodiment, the reactive material is a hydrogel that undergoes controlled volumetric expansion in response to changes in the environment, such as changes in pH or temperature (i.e., the hydrogel is "stimulus-expandable"). In an alternate embodiment, the at least one support member may be manufactured from or otherwise incorporate reactive material therein. The device is preferably controllably released from an elongate delivery apparatus. The release mechanism may be any of the vaso-occlusive device and stent detachment means known in the art including but not limited to mechanical, electrolytic, electro-mechanical, thermal, hydraulic, and shape-memory means.

In an alternate embodiment, the present invention is directed to a vascular patch comprising a radially and axially flexible patch body formed by a plurality of interlocking support members. The interlocking support members, which are capable of supporting vascular tissue, form a plurality of fenestrations. A reactive material capable of restricting or occluding the flow of blood to an aneurysm is selectively applied to, woven into, integral to, or otherwise incorporated into the interlocking support member. For example, the interlocking member may be manufactured from fibrous or formed reactive material In yet another embodiment, the present invention is directed to a coiled bridge device comprising radially and axially flexible resilient sinusoidal body member which defines a plurality of openings. The sinusoidal body member has a first radius of curvature R and a second radius of curvature R', wherein R' is larger than R. The sinusoidal body member is formed by at least one support member and has a reactive material capable of restricting or occluding the flow of blood to an aneurysm, selectively applied thereto.

In another embodiment, the present invention is directed to a helical stent having a radially and axially flexible cylindrical body member positioned between a first end and a second end. The cylindrical body member, which is formed by at least one support member capable of supporting vascular tissue, defines an internal lumen which is in communication with the first and second ends. A reactive material capable of restricting or occluding the flow of blood to an aneurysm is selectively applied to the at least one support member.

In yet another embodiment, the present invention is directed to a helical stent having a radially and axially flexible cylindrical body member positioned between a first end and a second end. The cylindrical body member, which is formed by at least one support member capable of supporting vascular tissue, defines an internal lumen which is in communication with the first and second ends. A reactive material capable of restricting or occluding the flow of blood to an aneurysm is selectively applied to the at least one support member.

In another embodiment, the present invention is directed to a reticulated expandable stent comprising radially and axially flexible cylindrical body member positioned between a first end and a second end. The cylindrical body member, which is formed by at least one support member capable of supporting vascular tissue, defines an internal lumen which is in communication with the first and second ends. A reactive material capable of restricting or occluding the flow of blood to an aneurysm is selectively applied to the at least one support member.

In still another embodiment, the present invention is directed to a bifurcated vascular support device comprising a bifurcated body member positioned between a first end, a second end, and a third end. The bifurcated body member further defines an internal lumen which communicates with the first, second, and third ends. The bifurcated body member is formed by at least one support member capable of supporting vascular tissue. A reactive material capable of restricting or occluding the flow of blood to an aneurysm is selectively applied to the at least one support member.

In another embodiment, the present invention is directed to an intra-aneurysmal bridge device comprising a flexible bridge body in communication with at least two engagement members. The at least two engagement members cooperatively form a joint. A reactive material capable of restricting or occluding the flow of blood to an aneurysm is selectively applied to the at least two engagement members.

The present invention also discloses a novel method of treating a vascular aneurysm. More particularly, the novel method of treating vascular aneurysms comprises the steps of providing a device for treating vascular aneurysms having a reactive material applied thereto, delivering the device to a vascular aneurysm, supporting the tissue near the aneurysm with the device, and allowing the reactive material to react thereby permitting the flow of blood through the blood vessel while restricting or occluding the flow of blood to the aneurysm.

Other objects and further features of the present invention will become apparent from the following detailed description when read in conjunction with the attached drawings.

BRIEF DESCRIPTION OF THE DRAWINGS

In the drawings:

FIG. 6 is a perspective view of an embodiment of the present invention comprising a vascular patch device useful in restricting the flow of blood to a vascular aneurysm;

FIG. 7 is another perspective view of an embodiment of the present invention comprising a vascular patch device useful in restricting the flow of blood to a vascular aneurysm;

FIG. 8 is a perspective view of the vascular patch device of the present invention positioned within a blood vessel proximate a vascular aneurysm;

FIG. 9 is a cross-sectional view of the vascular patch device of the present invention positioned within a blood vessel proximate a vascular aneurysm;

FIG. 10 is a perspective view of an embodiment of the present invention comprising a coiled bridge device useful in restricting the flow of blood to a vascular aneurysm;

FIG. 11 is a perspective view of another embodiment of the coiled bridge device useful in restricting the flow of blood to a vascular aneurysm;

FIG. 12 is a cross-sectional view of a coiled bridge device of the present invention positioned within a blood vessel proximate a vascular aneurysm;

FIG. 13 is a perspective view of an embodiment of the present invention comprising a helical stent device useful in restricting the flow of blood to a vascular aneurysm;

FIG. 14 is a perspective view of another embodiment of the helical stent device useful in restricting the flow of blood to a vascular aneurysm;

FIG. 15 is a cross-sectional view of a helical stent device of the present invention positioned within a blood vessel proximate a vascular aneurysm;

FIG. 16 is a perspective view of comprising a reticulated stent device useful in restricting the flow of blood to a vascular aneurysm;

FIG. 17 is a perspective view of another embodiment of the reticulated stent device useful in restricting the flow of blood to a vascular aneurysm;

FIG. 22 is a perspective view of an embodiment of the present invention positioned on an expandable balloon microcatheter within a blood vessel.

DETAILED DESCRIPTION OF THE INVENTION

Disclosed herein is a detailed description of various illustrated embodiments of the invention. This description is not to be taken in a limiting sense, but is made merely for the purpose of illustrating the general principles of the invention. The section titles and overall organization of the present detailed description are for the purpose of convenience only and are not intended to limit the present invention.

The aneurysm closure devices of the present invention are generally used to restrict the ability of blood flowing through a blood vessel from entering an aneurysm formed thereon. The devices disclosed herein may be applied to a blood vessel in a plurality of ways, including, without limitation, conventional surgical techniques and minimally invasive surgical techniques utilizing catheters of various sizes, balloon catheters, micro-catheters, and other ways generally known in the art of minimally invasive surgery. While the present invention may be used to repair a plurality of aneurysm at various locations throughout the body, the present invention is of particular value in procedures to repair or otherwise treat cerebrovascular aneurysms. The devices and methods of the present invention have particular compatibility with the materials and methods of manufacture and use disclosed in co-pending U.S. patent application Ser. No. 09/804,935 filed on Mar. 13, 2001 entitled "Hydrogels That Undergo Volumetric Expansion In Response To Changes In Their Environment And Their Methods Of Manufacture And Use", which has been assigned to the assignee of the present invention and which is incorporated by reference as if set forth herein in its entirety. Those skilled in the art will appreciate the present invention may be manufactured with a plurality of alternate reactive materials applied thereto, including, for example, collagen-polymer conjugate materials, photopolymerizable biodegradable materials, and other biodegradable cross-linked hydrogels known in the art.

Figure 1:
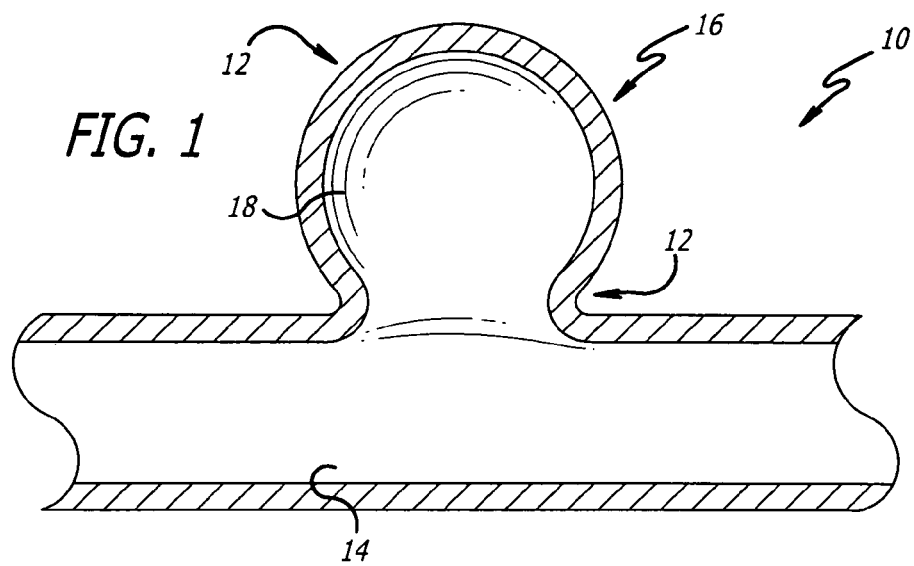
FIG. 1 is a cross-sectional view of a blood vessel having an vascular aneurysm formed on its wall.

Aneurysms form as a result of outward pressure applied to a diseased or damaged blood vessel wall by blood flowing within the vessel, thereby resulting in a weakened section of tissue ballooning outwardly from a blood vessel. FIG. 1 shows an aneurysm 10 comprising a neck portion 12 in communication with a blood vessel 14 and having a dome portion 16 defining aneurysm cavity 18. Those skilled in the art will appreciate FIG. 1 illustrates an exemplary vascular aneurysm and is not intended to limit the scope or intent of the present invention.

Figure 2:
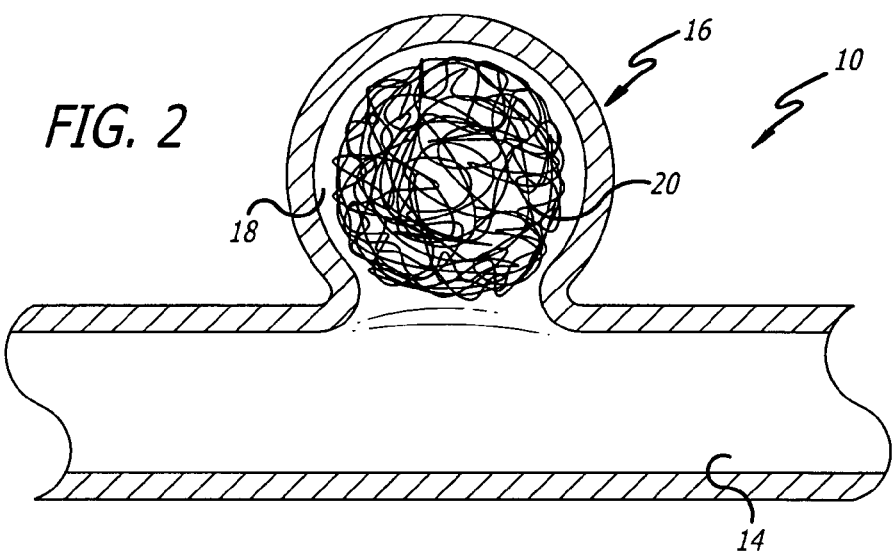
FIG. 2 is a cross-sectional view of a prior art method of treating vascular aneurysm requiring the deposition of material within the vascular aneurysm.
Figure 3:
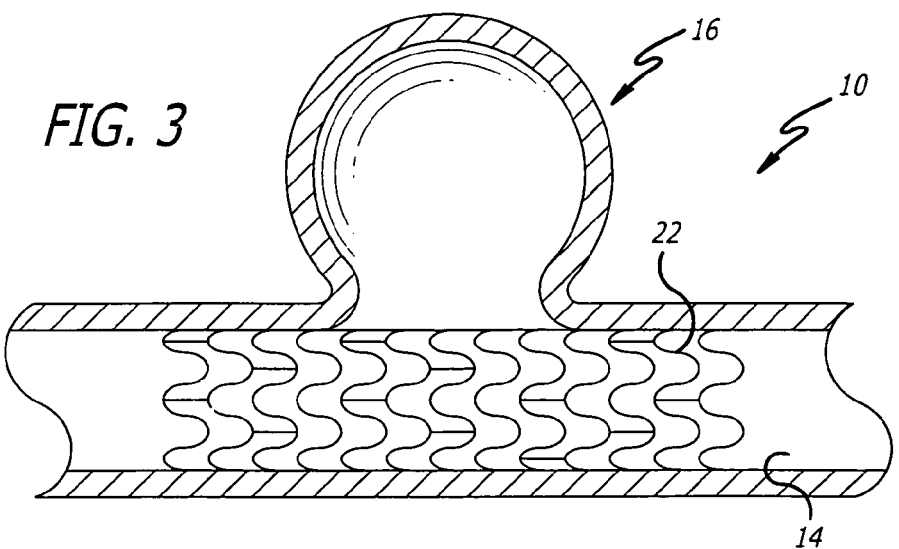
FIG. 3 is a cross-sectional view of an alternate prior art method of treating vascular aneurysm wherein a mechanical stent is positioned near the aneurysm.

One method of treating aneurysm requires the formation of an embolism proximate to or within the aneurysm, thereby restricting or depriving the aneurysm of blood flow and reducing the likelihood the aneurysm will rupture. FIGS. 2 and 3 show prior art devices used to repair aneurysms by artificially creating embolisms within or proximate to the aneurysm. In FIGS. 2 and 3 the reference numerals 10, 12, 14, 16, and 18 have analogous meanings to the reference numerals identifying the features of FIG. 1. FIG. 2 shows an aneurysm 10 in communication with a blood vessel 14. As shown, a vaso-occlusive device 20 is positioned within the aneurysm cavity 18. Typically, a micro-catheter or other device is used to inject or otherwise insert the vaso-occlusive device 20 into the aneurysm cavity 18, thereby decreasing the volume of the aneurysm capable of receiving blood from the blood vessel 14. FIG. 3 shows an alternate device used treat aneurysms. As shown in FIG. 3, a stent 22 is positioned within a blood vessel 14 proximate to an aneurysm 10. A stent 22 is a mechanical scaffold used to provide support to otherwise incompetent or weakened tissue, or to or maintain the patency of a narrowed or occluded blood vessel.

Figure 4:
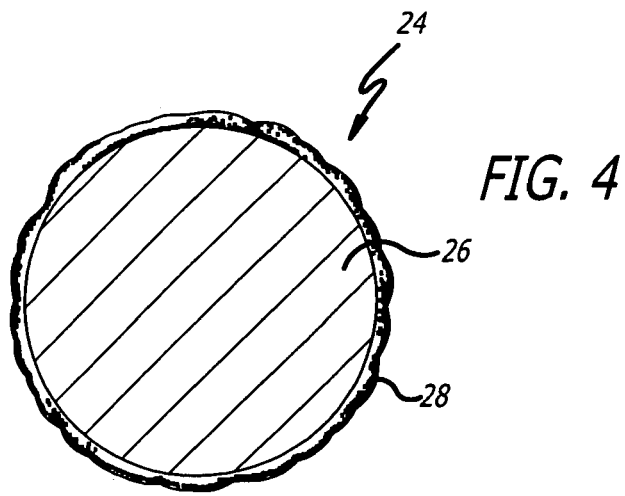
FIG. 4 is sectional view of a support member of the present invention having non-reacted reactive material disposed thereon.
Figure 5A:
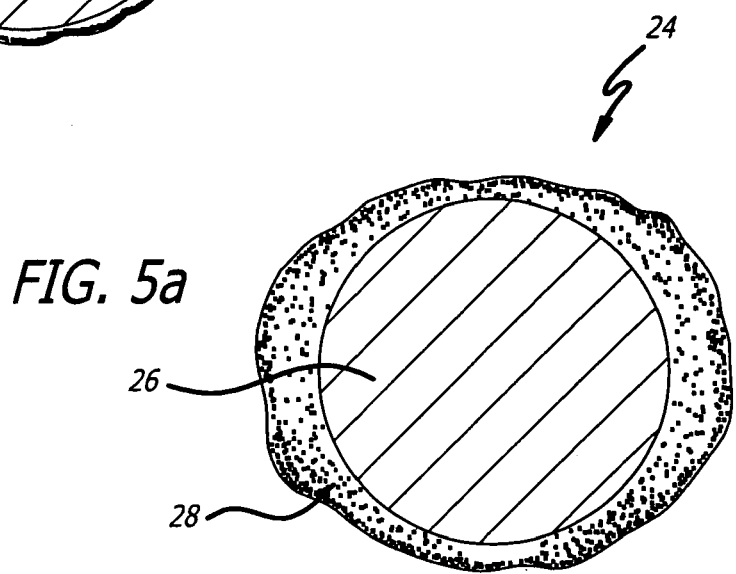
FIG. 5a is sectional view of a support member of the present invention having reacted reactive material disposed thereon.
Figure 5B:
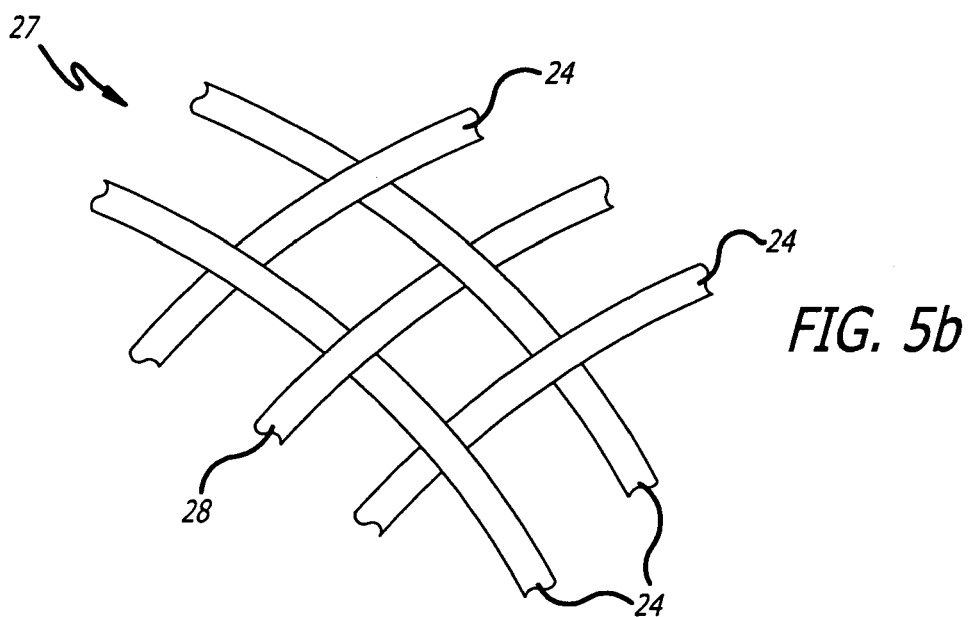
FIG. 5b is a perspective view of an embodiment of the present invention comprising a structure having reactive material interwoven therein.

The present invention discloses a plurality of devices useful for the embolization or isolation of aneurysms. More particularly, the present invention discloses various structures capable of implantation within a plurality of blood vessels of various sizes. Disclosed herein are various neck bridges, vascular patches, and stents which are generally comprised of a series of interlocking or otherwise connected support members forming a predetermined shape. FIGS. 4 and 5a show cross sectional views of a portion of a support member 24 before and following implantation as used in a plurality of embodiments of the present invention. As shown in FIG. 4, the support member 24 may comprise a device substrate 26 having a reactive coating or materials 28 applied to the exterior portion prior to implantation. FIG. 5a shows reactive coating 28 disposed on the support member 24 in a reacted state, wherein the reactive coating 28 has expanded outwardly from the device substrate 26 in a preferential direction. In the illustrated embodiment, the reactive coating 28 has expanded more along the horizontal axis than the vertical axis. Those skilled in the art will appreciate that the support member 24 of the present invention may be manufactured from a plurality of biologically-compatible materials, including, for example, platinum, gold, tantalum, titanium, stainless steel, tungsten, Nitinol, shape memory alloys, formed reactive material, or other suitable material. FIG. 5b shows an alternate embodiment of the present invention comprising a reactive material strand 28 woven with support members 24, thereby forming an interwoven structure 27. Those skilled in the art will appreciate the reactive strands 28 may positioned within the interwoven structure 27 in a radial, axial, or radially and axial orientation. In an alternate embodiment, the device substrate 26 of the present invention may be manufactured from a plurality of biologically-compatible polymer materials, including, but not limited to, polyurethane, polyvinyl alcohol, polyester, polytetrafluoroethylene, silicone, acrylic, or similar polymeric material. In yet another embodiment, the support member 24 may incorporate radio-opaque or echogenic materials or agents, thereby enabling the surgeon to precisely position the device within a blood vessel or other hollow organ. Those skilled in the art will appreciate that the support member 24, device substrate 26, and/or the reactive coating 28 may be chemically doped or impregnated with a drug or growth-promoting material to encourage tissue growth or impart other therapeutic benefit about the support member 24.

The reactive coating or material 28 may be fabricated from a plurality of materials capable of expanding or volumetrically changing over time within the presence of blood or other fluid. In a preferred embodiment, the applicant's co-pending U.S. patent application Ser. No. 09/804,935 filed on Mar. 3, 2001 entitled "Hydrogels That Undergo Volumetric Expansion In Response To Changes In Their Environment And Their Methods Of Manufacture And Use" discloses a stimulus-expandable hydrogel which is particularly useful as a reactive coating or material 28 for treating aneurysms. The stimulus-expandable hydrogel can be prepared by forming a liquid reaction mixture that contains a) monomer(s) and/or polymer(s) at least portion(s) of which are sensitive to environmental changes (e.g., changes in pH or temperature), b) a crosslinker and c) a polymerization initiator. If desired, a porosigen, (e.g., sodium chloride, ice crystals, and sucrose) may be incorporated into the liquid reaction mixture. Porosity is formed by the subseauent removal of the porosigen from the resultant solid hydrogel (e.g., by repeated washing). Typically, a solvent will also be used to dissolve solid monomer(s) and/or polymers. However, in cases where only liquid monomers are used, there may be no need for inclusion of a solvent. Generally, the controlled rate of expansion of the present invention is imparted through the incorporation of ethylenically unsaturated monomers with ionizable functional groups, (e.g. amines, carboxylic acids). For example, if acrylic acid is incorporated into the crosslinked network, the hydrogel is incubated in a low pH solution to protonate the carboxylic acids. After the excess low pH solution has been rinsed away and the hydrogel dried, the hydrogel can be introduced through a microcatheter filled with saline at physiological pH or blood. The hydrogel cannot expand until the carboxylic acid groups deprotonate. Conversely, if an amine containing monomer is incorporated into the crosslinked network, the hydrogel is incubated in a high pH solution to deprotonate amines. After the excess high pH solution has been rinsed away and the hydrogel dried, the hydrogel can be introduced through a microcatheter filled with saline at physiological pH or blood. The hydrogel cannot expand until the amine groups protonate.

In one embodiment, the above above-referenced stimulus-expandable hydrogel comprises 1.52 g (0.021 moles) acrylamide, 0.87 g (0.009 moles) sodium acrylate, 0.005 g (0.00003 moles) N,N-methylenebisacrylamide. 7.95 g water, and 4.5 g sodium chloride (<10 micron particle size) added to an amber jar. The initiators, 53 microliters of N,N,N',N-tetramethylethylenediamine and 65 microliters of 20% w/w ammonium persulfate in water, are added and the solution is aspirated into a 3-cc syringe. The solution is then injected into 0.025" ID tubing and allowed to polymerize for 2 hours. and dried in a vacuum oven. The dried hydrogel is washed 3 times in distilled water for 10-12 hours, 2 hours, and two hours, respectively, to remove porosigen, any unreacted monomer and any unincorporated monomers. The hydrogel may be drawn or formed into fibrous strands or portions of similar size and dimension as the support members 24. These strands are then hydrated in alcohol and dried under vacuum at approximately 55 C for about 2 hours. Thereafter, the dried hydrogel is placed in 50% hydrochloric acid/50% water and incubated for about 70 hours at 37 C. After the incubation, the excess hydrochloric acid solution is rinsed off of the pellets or strands with consecutive rinses of a) 70% isopropyl alcohol: 30% water for about 5minutes, b) 100% isopropyl alcohol for about 15 minutes, c) 100% isopropyl for about 15 minutes and d) 100% isopropyl alcohol for about 15 minutes. The hydrogel is then dried under vacuum at 55 C for at least 2 hours. Prior to or following the complete drying process, the hydrogel may be selectively applied to the at least one support member 24 as desired in a plurality of ways. If desired, the hydrogel strands may be utilized as support members 24 without reinforcement. Thereafter, the hydrogel may be selectively applied to a support member in a plurality of manners. In one embodiment, the reactive material is applied to the entire surface of a support member 24. In an alternate embodiment, the reactive material is selectively applied to a portion of the support member 24. For example, the reactive material may be selectively applied to the portion of a support member 24 which will engage a wall of a blood vessel. Once implanted in vivo, the hydrogel of the present embodiment becomes fully swollen (to diameters of about 0.035 inch) after approximately one hour at physiological pH (about 7.4). Alternatively, the hydrogel strands may be woven, or integrated into the support structure. In addition, the support structure may be manufactured from hydrogel material.

FIGS. 6-9 show an embodiment of the present invention useful in isolating an aneurysm from a blood vessel. As shown in FIG. 6, the present embodiment discloses a vascular patch device 30 comprising a body member 32 formed by a plurality of interwoven or otherwise joined support members 24 axially displaced in relation to each other, capable of supporting weakened vascular tissue. The interwoven support members 24 form a plurality of fenestrations 34. As shown in FIGS. 6-8, a reactive coating 35 is selectively applied to the interwoven support members 35. Those skilled in the art will appreciate the present embodiment permits the isolation and embolization of an aneurysm formed on a blood vessel without substantially occluding blood flow through the blood vessel. As shown in FIG. 7 the vascular patch device 30 formed by the plurality of support members 24 has an arcuate profile 36. The arcuate profile 36 may be selected to approximate the radius of curvature of the receiving blood vessel, thereby further limiting blood vessel occlusion following implantation. Those skilled in the art will appreciate the vascular patch device 30 of the present invention may be manufactured in a plurality of sizes. For example, the vascular patch device 30 may approximate 270 degrees of the receiving blood vessel, thereby using mechanical force to secure the device within the blood vessel. If desired, the vascular patch device 30 may incorporate malleable support members 24, thereby permitting the surgeon to adjust the arcuate profile 36 to conform to the radius of curvature of the receiving blood vessel during implantation. In FIG. 8 the reference numerals 10, 12, 14, 16, and 18 have analogous meanings to the reference numerals identifying the features of FIG. 1. FIG. 8 shows a vascular patch device 30 positioned within a blood vessel 14 proximate to an aneurysm 10, wherein the device 30 traverses the opening 38 to the aneurysm cavity 18 formed by the neck portion 12. As shown in FIG. 8, the swelling of the reactive coating 35 decreases the sizes of the plurality of fenestrations 34 formed in the vascular patch device 30, thereby reducing the amount of blood entering the aneurysm. In an alternate embodiment, the device 30 may include a plurality of attachment devices (not shown) to assist in implanting and securing the device within a blood vessel. The attachment devices may include, for example, hooks, barbs, or similar devices manufactured from a plurality of materials, such as platinum, gold, tantalum, titanium, stainless steel, Nitinol, or other suitable material. In an alternate embodiment, the vascular patch device 30 may incorporate alternate attachment mechanisms, including, without limitation, adhesive materials, mechanical attachment mechanisms, or vacuum attachment mechanisms. FIG. 9 shows a cross sectional view of a blood vessel 14 having the vascular patch device 30 of the present embodiment positioned proximate to an aneurysm. Those skilled in the will appreciate the present embodiment may be manufactured in a plurality of sizes, thereby enabling usage in various blood vessels to repair a plurality of aneurysms.

FIGS. 10-12 show an alternate embodiment of the present invention useful in treating aneurysms. As shown in FIG. 10, the present embodiment discloses a resilient coiled bridge device 40 comprising a sinusoidal body member 42 defining a plurality of openings 44. The body member 42 may be formed along an arc 46, thereby aiding in the implantation of the device while limiting the occlusion of blood vessel. The resilient body member 42 may be compressed along the line 48 to enable delivery and positioning of the coiled bridge device 40 in vivo. Upon placement of the coiled bridge device 40 the resiliency of body member 42 exerts an outward pressure along line 50, wherein the resilient body member 42 engages the blood vessel wall (not shown). In an alternate embodiment, the coiled bridge device 40 may be used to provide mechanical support to weakened vascular tissue. As shown in FIG. 10, the body member 42 is coated with or otherwise disposes a reactive coating, thereby occluding or otherwise inhibiting the flow of blood to the aneurysm. FIG. 11 shows an alternate embodiment of the coiled bridge device 40, comprising a resilient sinusoidal body member 42 having at least one reactive section 52 disposed thereon, and defining a plurality of openings 44. The reactive portions 52 are areas selectively coated or otherwise incorporating a reactive material as defined above. Those skilled in the art will appreciate the present embodiment permits the embolization of the aneurysm while limiting the occlusion within the blood vessel. FIG. 12 shows a cross sectional view of the present embodiment positioned within a blood vessel 14, wherein the at least one reactive section 52 occludes or inhibits blood flow to an aneurysm 10.

FIGS. 13-15 show yet another embodiment of the present invention useful in treating aneurysms formed on weakened vascular tissue. FIGS. 13-15 show various expandable devices, commonly referred to as "stents", capable of embolizing or isolating an aneurysm formed on weakened blood vessel tissue. In an alternate embodiment, the intraluminal vascular prosthetic devices of the present invention may be used to provide mechanical support to weakened vascular tissue. As shown in FIG. 13, the helical expandable stent 54 comprises a first end 56 and a second end 58, having cylindrical body member 60 disposed therebetween. The cylindrical body member 60 defines a central lumen 62 co-axially aligned with the longitudinal axis 64 of the stent 54. The helical expandable stent 54 has a first diameter, D, thereby enabling insertion and positioning of the device within a blood vessel, and a larger second diameter, D', which is capable of engaging and supporting a blood vessel wall. As shown, a reactive material is selectively applied to the external surface of the helical expandable stent 54. FIG. 14 shows an alternate embodiment of the helical expandable stent 54, comprising a cylindrical body member 60 having a first end 56 and a second end 58. The cylindrical body member 60 further comprises at least one reactive section 66 disposed thereon, thereby enabling the embolization or isolation of an aneurysm while limiting blood vessel occlusion. FIG. 15 shows cross sectional view of the present embodiment positioned within a blood vessel 14, wherein the at least one reactive section 66 occludes or otherwise inhibits blood flow to an aneurysm 10.

Figure 18:
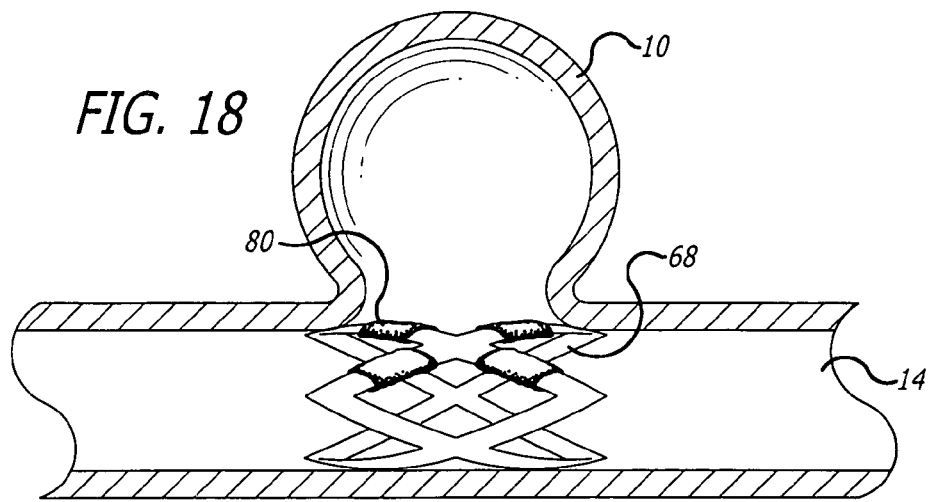
FIG. 18 is a cross-sectional view of a reticulated stent device of the present invention positioned within a blood vessel proximate a vascular aneurysm.

In yet another embodiment, FIGS. 16-18 show various embodiments of reticulated expandable intraluminal stents. As shown in FIGS. 16 and 17, the reticulated stent 68 comprises a first end 70 and a second end 72, having a cylindrical reticulated body 74 positioned therebetween. The cylindrical reticulated body 74, which is comprised of a series of interconnected support members 24, defines a flow lumen 76 co-axially aligned along the longitudinal axis 78 of the stent 68 having a first compacted diameter D, and a second larger diameter D'. As shown in FIGS. 16-18, a reactive material may be applied to the external portion of the stent 68. Alternatively, the reactive material may be applied to selected areas or individual support members 24 may be manufactured from reactive material or otherwise incorporated therein. FIG. 18 shows an embodiment of the reticulated expandable stent 68 positioned within a blood vessel 14, wherein a reactive section 80 is occluding or otherwise inhibiting the flow of blood to an aneurysm 10.

Figure 19:
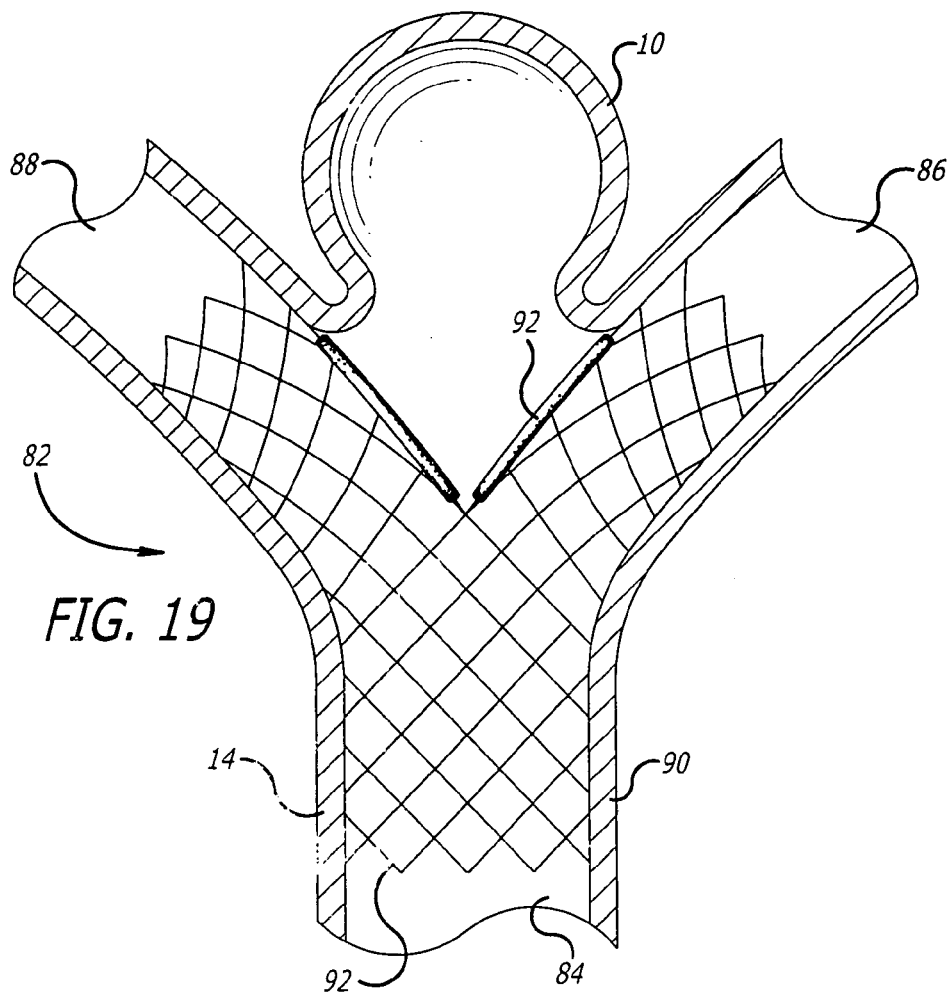
FIG. 19 is a cross-sectional view of an embodiment of the present invention comprising a bifurcated stent device positioned within a blood vessel proximate a vascular aneurysm.

FIG. 19 shows yet another embodiment of the present invention. As shown in FIG. 19, the occlusive bifurcated support 82 comprises a first end 84, a second end 86, and a third end 88 and having a cylindrical body 90 positioned between the first, second, and third ends. The cylindrical body 90 further defines an internal lumen 92, which is in communication with the first, second, and third ends, 84, 86, and 88, respectively. The occlusive bifurcated support 82 has first diameter D, thereby enabling insertion and positioning of the device within a blood vessel, and a larger second diameter D', which is capable of engaging a blood vessel wall. As such, the cylindrical body 90 may be manufactured from a plurality of interlocking or otherwise joined support members 24, and may be reticulated. As shown in FIG. 19, reactive material 92 is incorporated into the cylindrical body 82, thereby occluding the aneurysm 10 formed on the blood vessel 14.

Figure 20:
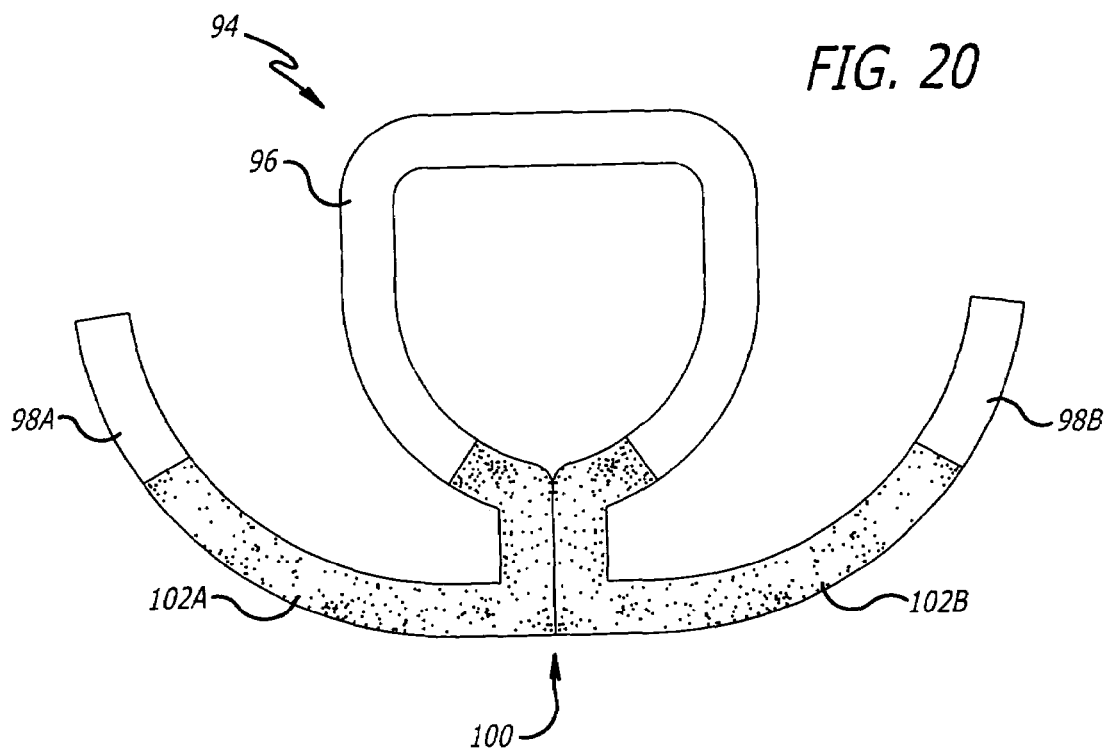
FIG. 20 is a cross-sectional view of an intra-aneurysmal bridge device of the present invention useful in restricting the flow of blood to a vascular aneurysm.
Figure 21:
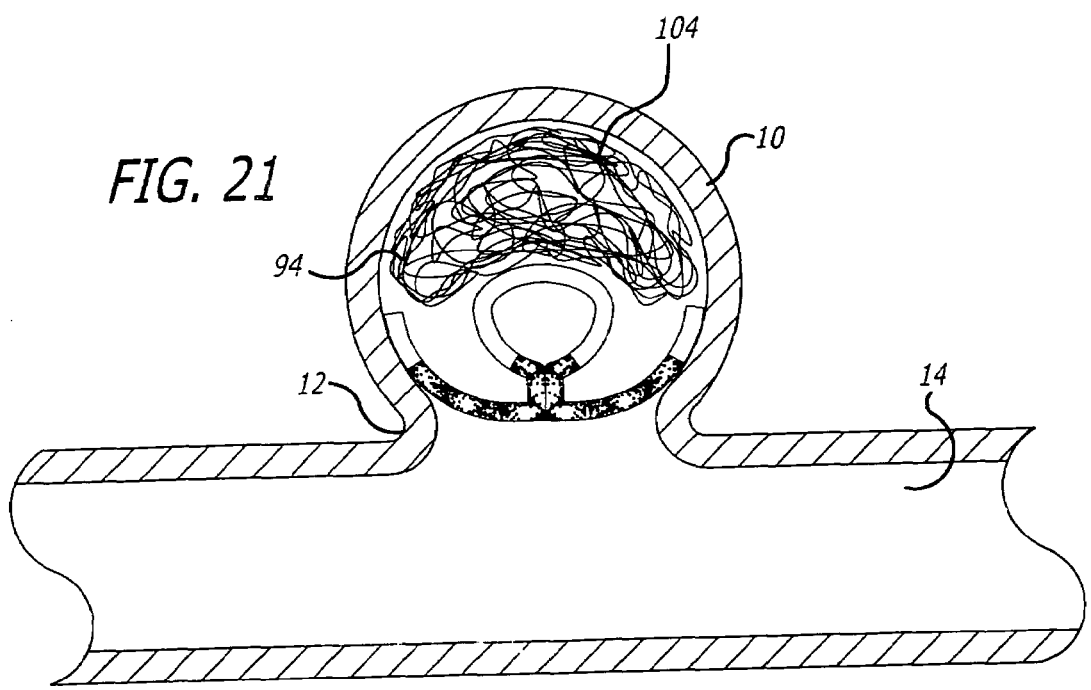
FIG. 21 is a cross-sectional view of an intra-aneurysmal bridge device of the present invention positioned within a vascular aneurysm.

FIGS. 20 and 21 show another embodiment of the present invention, disclosing an intra-aneurysmal neck bridge structure 94 positioned near the neck portion 12 of an aneurysm 10. As shown, the intra-aneurysmal neck bridge structure 94 comprises device body 96 in communication with at least two engagement members 98A and 98B cooperatively forming a device joint 100. Those skilled in the art will appreciate the device joint 100 may sealably isolate the aneurysm from the flow of blood through the blood vessel. The engagement members 98A-B are formed to approximate the radius of curvature of the aneurysm thereby providing an interface between the device and the aneurysm. Reactive portions 102A-B are positioned on the engagement members 98A-B, respectively. As shown in FIG. 21, a material 104 may be inserted into the aneurysm prior to or after applying the intra-aneurysmal neck bridge structure 94. Such material 104 may include, for example, a plurality of materials such as hydrogels, hog hair, microfibrillar collagen, various polymeric agents, material suspensions, metallic or radio-opaque materials, and other space filling materials.

The present invention further discloses a method of treating vascular aneurysms. In the one embodiment, the present invention discloses a method of percutaneously inserting a aneurysmal treatment device into a blood vessel, advancing the treatment device to a location proximate to a vascular aneurysm, and applying the device to the aneurysm or surrounding tissue without substantially restricting blood flow through the blood vessel. The apparatus of the present invention may be delivered to a situs in vivo in a plurality of manners, including, for example, on guidewires, balloon catheters or through micro-catheters. FIG. 22 shows an exemplary embodiment 104 of the present invention being applied to an aneurysm 10 using a balloon micro-catheter 106.

In practice, the surgeon positions a device, for example, an expandable reticulated stent 104 on a delivery device, for example, a micro-balloon catheter 106. Thereafter, a first incision is made proximate a blood vessel and a guidewire 108 is inserted therein. Commonly, the guidewire will enter the circulatory system through the femoral artery, the femoral vein, the jugular vein, the carotid artery, or a similar blood vessel. The guidewire 108 may then be directed through the circulatory system to a location proximate to the aneurysm 10 and, thereafter, made to exit the body through a remote exit point. The delivery device 106 and stent 104 may then be advanced along the guidewire 108 and positioned proximate to the aneurysm 10. Typically, visualization methods, such as fluoroscopy, ultrasound visualization, or echogenic location are utilized to precisely position the delivery device near or within the aneurysm 10. Once positioned, the micro-balloon 106 is inflated and the expandable reticulated stent 104 is applied to the tissue. The portion of the expandable reticulated stent 104 disposing the reactive material 110 is positioned proximate to the aneurysm. Thereafter, the delivery device 106 and guidewire 108 are removed from the body. The activation of the reactive material 110 selectively applied to the stent 104 restricts or occludes the flow of blood to the aneurysm 10. The activation process may result from a plurality of occurrences, including, for example, the presence of a physiological pH for an extended period, the presence of an enzyme or other material within the blood, electromagnetic-activation resulting from the introduction of a predetermined wavelength of electromagnetic energy. The procedure above discloses one such activation method, however, other activation methods known in the art are contemplated.

In closing it is understood that the embodiments of the invention disclosed herein are illustrative of the principles of the invention. Other modifications may be employed which are within the scope of the invention. Accordingly, the present invention is not limited to that precisely as shown and described in the present invention.

What is claimed is:

1. A method of treating a vascular aneurysm, comprising:
providing an expandable support device having a substantially cylindrical body member located between a first and second end, said cylindrical body member having at least one circumferential element between said first and said second end defining an internal lumen in communication with said first and second ends, said support device having fenestrations and a reactive material selectively applied to not all of the fenestrations of said support device, wherein blood is capable of flowing through said internal lumen and flowing radially through said fenestrations into the aneurysm;
delivering the device to a vascular aneurysm from within a blood vessel;
supporting tissue proximate said aneurysm with said device; permitting blood to flow through said blood vessel, some of the blood flowing radially outward through said fenestrations; and
activating said reactive material disposed on said device to increase the resistance to blood flow through certain fenestrations of said support device to the aneurysm.

2. The method of claim 1 wherein said step of activating said reacting material occurs in the presence of a physiological pH of about 7.4.

3. The method of claim 1 wherein said step of activating said reactive material further comprises the step of volumetrically expanding said reacting material.

4. The method of claim 1 wherein said step of delivering the device further comprises using a catheter to deliver said device to said aneurysm.

5. The method of claim 1 wherein said step of using a catheter to deliver said device to said aneurysm further comprises using a balloon catheter to deliver said device to said aneurysm.

6. The method of claim 1 further comprising inserting said device into said aneurysm.

7. A method of treating a vascular aneurysm, comprising:
providing an expandable support device having fenestrations and a stimulus-expandable hydrogel selectively applied to the support device adjacent to some but not all of the fenestrations, said stimulus expandable hydrogel having a first state of protonation prior to implantation in the blood vessel and undergoing a predetermined controlled rate of change to a second state of protonation after implantation in the blood vessel in contact with blood, said change in the state of protonation of the hydrogel giving rise to expansion of the hydrogel, said support device being implantable in a blood vessel adjacent to the aneurysm;
implanting the support device in a blood vessel adjacent to the aneurysm;
permitting blood to flow through said blood vessel, some of the blood flowing radially outward through said fenestrations and contacting the hydrogel; and
allowing the hydrogel to change from its first state of protonation to its second state of protonation, thereby resulting in expansion of the hydrogel and lessening of the size of the adjacent fenestrations, and thereby increasing the resistance to blood flow through those fenestrations to the aneurysm.

8. The method of claim 7 wherein said step of activating said stimulus-expandable hydrogel occurs in the presence of a physiological pH of about 7.4.

9. The method of claim 8, wherein said ionizable functional group comprises an amine.

10. The method of claim 8, wherein said ionizable functional group comprises carboxylic acid.

11. The method of claim 7 wherein said step of activating said stimulus-expandable hydrogel further comprises the step of volumetrically expanding said stimulus-expandable hydrogel.

12. The method of claim 7, wherein said stimulus-expandable hydrogel applied to said fenestrations comprises at least an ethylenically unsaturated monomer with an ionizable functional group.

* * * * *